United States Patent
Ressler et al.

(10) Patent No.: US 10,314,835 B2
(45) Date of Patent: Jun. 11, 2019

(54) METHODS OF MANAGING CONDITIONED FEAR WITH NEUROKININ RECEPTOR ANTAGONISTS

(71) Applicant: Emory University, Atlanta, GA (US)

(72) Inventors: Kerry J. Ressler, Atlanta, GA (US); Raul Andero Gali, Barcelona (ES)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/320,952

(22) PCT Filed: Jun. 25, 2015

(86) PCT No.: PCT/US2015/037629
§ 371 (c)(1),
(2) Date: Dec. 21, 2016

(87) PCT Pub. No.: WO2015/200594
PCT Pub. Date: Dec. 30, 2015

(65) Prior Publication Data
US 2017/0296528 A1   Oct. 19, 2017

Related U.S. Application Data

(60) Provisional application No. 62/016,683, filed on Jun. 25, 2014.

(51) Int. Cl.
*A61K 31/4545* (2006.01)
*A61K 45/06* (2006.01)

(52) U.S. Cl.
CPC .......... *A61K 31/4545* (2013.01); *A61K 45/06* (2013.01)

(58) Field of Classification Search
CPC ............................ A61K 31/4545; A61K 45/06
See application file for complete search history.

(56) References Cited

U.S. PATENT DOCUMENTS

| | | | |
|---|---|---|---|
| 6,420,388 B1 * | 7/2002 | Ennonds-Alt | A61K 31/4545 514/316 |
| 7,521,449 B2 | 4/2009 | Emonds-Alt | |
| 2008/0261976 A1 | 10/2008 | Emonds-Alt | |
| 2012/0157450 A1 | 6/2012 | Craig | |

FOREIGN PATENT DOCUMENTS

| | | |
|---|---|---|
| EP | 1192952 | 3/2003 |
| WO | 2002053140 | 7/2002 |
| WO | 2004056364 | 7/2004 |
| WO | 2004056805 | 7/2004 |

OTHER PUBLICATIONS

Giuseppe et al, Exp. Opin. Ther. Patents, 1997, 7(4): 307-323.*
Kronenberg et al, Pharmacopsychiatry, 38(1), 24-29 (Year: 2005).*
Andero et al. A Role for Tac2, NkB, and Nk3 Receptor in Normal and Dysregulated Fear Memory Consolidation, Neuron, 2014, 83, 444-454.
Andero et al. Amygdala-Dependent Molecular Mechanisms of the Tac2 Pathway in Fear Learning, Neuropsychopharmacology (2016) 41, 2714-2722.
Brenes et al. Involvement of midbrain tectum neurokinin-mediated mechanisms in fear and anxiety, Braz J Med Biol Res, 2012, vol. 45(4) 349-356.
Daoui et al. A Tachykinin NK3 Receptor Antagonist, SR 142801 (Osanetant), Prevents Substance P-induced Bronchial Hyperreactivity in Guinea-pigs, Pulmonary Pharmacology & Therapeutics (1997) 10, 261-270.
Dunlop et al. Pharmacological Innovations for Posttraumatic Stress Disorder and Medication-Enhanced Psychotherapy, Current Pharmaceutical Design, 2012, 18, 5645-5658.
Ebner et al. Tachykinin Receptors as Therapeutic Targets in Stress-Related Disorders, Current Pharmaceutical Design, 2009, 15, 1647-1674.
Gariepy et al. Blockade of tachykinin NK3 receptor reverseshypertension through a dopaminergic mechanism in the ventral tegmental area of spontaneously hypertensive rats, British Journal of Pharmacology (2010) 161 1868-1884.
Kronenberg et al. Randomized, double-blind study of SR142801 (Osanetant). A novel neurokinin-3 (NK3) receptor antagonist in panic disorder with pre- and posttreatment cholecystokinin tetrapeptide (CCK-4) challenges, Pharmacopsychiatry, 2005, 38(1):24-9.
Steinhoff et al. Tachykinins and Their Receptors: Contributions to Physiological Control and the Mechanisms of Disease, Physiol Rev. 2014, 94(1): 265-301.
Andero et al. The Role of Tac2 gene and Nk3 receptor in fear memory consolidation, 2012, Neuroscience Meeting Planner. New Orleans, LA: Society for Neuroscience, 2012.
Andero et al. A Role for the Tac2 Gene and NK3 Receptor in Fear Memory Consolidation Biol Psychiatry 2013, 73:34S.
Extended European Search Report for EP Application No. 15811219. 3, dated Oct. 11, 2017.

* cited by examiner

*Primary Examiner* — Sudhakar Katakam
(74) *Attorney, Agent, or Firm* — Emory Patent Group

(57) ABSTRACT

This disclosure relates to managing conditioned fear and conditions induced by experiencing or witnessing an extreme traumatic event using neurokinin receptor antagonists. In certain embodiments, the disclosure relates to methods of treating or preventing conditioned fear comprising administering an effective about neurokinin 3 receptor antagonist to a subject in need thereof. In certain embodiments, the subject is diagnosed with Post-Traumatic Stress Disorder. In certain embodiments, the neurokinin 3 receptor antagonist is (R)—N-{{3-[1-Benzoyl-3-(3,4-dichlorophenyl)piperidin-3-yl]prop-1-yl}-4-phenylpiperidin-4-yl}-N-methylacetamine or salts thereof.

7 Claims, 10 Drawing Sheets

METHODS OF MANAGING CONDITIONED FEAR WITH NEUROKININ RECEPTOR ANTAGONISTS

CROSS-REFERENCE TO RELATED APPLICATIONS

This application is the National Stage of International Application Number PCT/US2015/037629 filed Jun. 25, 2015, which claims the benefit of priority to U.S. Provisional Application No. 62/016,683 filed Jun. 25, 2014. The entirety of each of these applications is hereby incorporated by reference for all purposes.

STATEMENT REGARDING FEDERALLY FUNDED RESEARCH

This invention was made with government support under Grant MH101492 and MH096764 awarded by the National Institutes of Health. The government has certain rights in the invention.

BACKGROUND

Symptoms of Post-Traumatic Stress Disorder (PTSD) include re-experiencing memories of a traumatic event such as through intrusive thoughts, flashbacks, and nightmares. PTSD is also typically accompanied by hyperarousal symptoms. Moreover, persistent highly aversive memories related to the trauma, potentially over-consolidated memories, and the inability of these memories to be extinguished are all frequent characteristics of this disorder. Specifically relevant is the memory consolidation phase following emotional learning since it is required to stabilize the initial fear memory trace. FDA-approved pharmaceutical treatments for PTSD are antidepressants which have met with limited results in clinical trials. Thus, more effective, targeted approaches to prevention and treatment of PTSD are needed. Dunlop, et al. report pharmacological interventions for post-traumatic stress disorder and medication enhanced psychotherapy. Current pharmaceutical design, 2012, 18, 5645-5658.

Ebner et al. report tachykinin receptors as therapeutic targets in stress-related disorders. Curr Pharm Des, 2009, 15(14): 1647-74.

Daoui et al. report a tachykinin NK3 receptor antagonist, osanetant, prevents substance P-induced bronchial hyper-reactivity in guinea-pigs. Pulm Pharmacol Ther, 1997, 10(5-6):261-70.

Emonds-Alt et al., report osanetant in the treatment of depression and depressive disorders. See also U.S. Pat. No. 6,420,388.

Kronenberg et al. report randomized, double-blind study of osanetant in panic disorder induced with cholecystokinin tetrapeptide (CCK-4) challenges. Pharmacopsychiatry, 2005, 38(1):24-9.

See also U.S. Pat. No. 7,521,449, WO2004/056805, WO2004/056364, WO2002053140, U.S. App. 2008/026197.

References cited herein are not an admission of prior art.

SUMMARY

This disclosure relates to managing conditioned fear and conditions induced by experiencing or witnessing a traumatic event using neurokinin receptor antagonists. In certain embodiments, the disclosure relates to methods of treating or preventing conditioned fear comprising administering an effective about neurokinin 3 receptor antagonist to a subject in need thereof. In certain embodiments, the subject is diagnosed with Post-Traumatic Stress Disorder (PTSD). In certain embodiments, the neurokinin 3 receptor antagonist is (R)—N-{{3-[1-Benzoyl-3-(3,4-dichlorophenyl)piperidin-3-yl]prop-1-yl}-4-phenylpiperidin-4-yl}-N-methylacetamine or salts thereof.

In certain embodiments, the neurokinin 3 receptor antagonist is administered in combination with a second active agent such as an anti-depressant. In certain embodiments, the agent is sertraline, paroxetine, fluoxetine, citalopram, baclofen, modafinil, eszopiclone, hydrocortisone, varenicline, dexamethasone or combinations thereof.

In certain embodiments, the neurokinin 3 receptor antagonist is administered within an hour of or within a day of experiencing a traumatic event.

In certain embodiments, the neurokinin 3 receptor antagonist is administered at the time of or within an hour of psychotherapy, cognitive behavioral therapy, exposure therapy, cognitive restructuring, or stress inoculation training.

BRIEF DESCRIPTION OF THE DRAWINGS

FIG. 6A) Osanetant did not modified anxiety-like behavior as shown by the time in the center of the open field.

FIG. 6B) Animals receiving vehicle or osanetant showed equivalent distance traveled in the open field which indicates similar levels of locomotor activity.

FIG. 6C, D and E) Osanetant did not modified anxiety-like behavior as shown by

FIG. 6C time in open arms,

FIG. 6D entries in open arms, and

FIG. 6E time in closed arms in the elevated plus maze.

FIG. 6F) Equivalent shock reactivity shown when vehicle or osanetant was given 30 minutes before testing in the startle chamber.

FIG. 6G) Osanetant given systemically 30 minutes before FC impairs fear memory consolidation, without affecting fear expression, as shown by decreased freezing in the fear expression test.

DETAILED DESCRIPTION

Figure 1A:
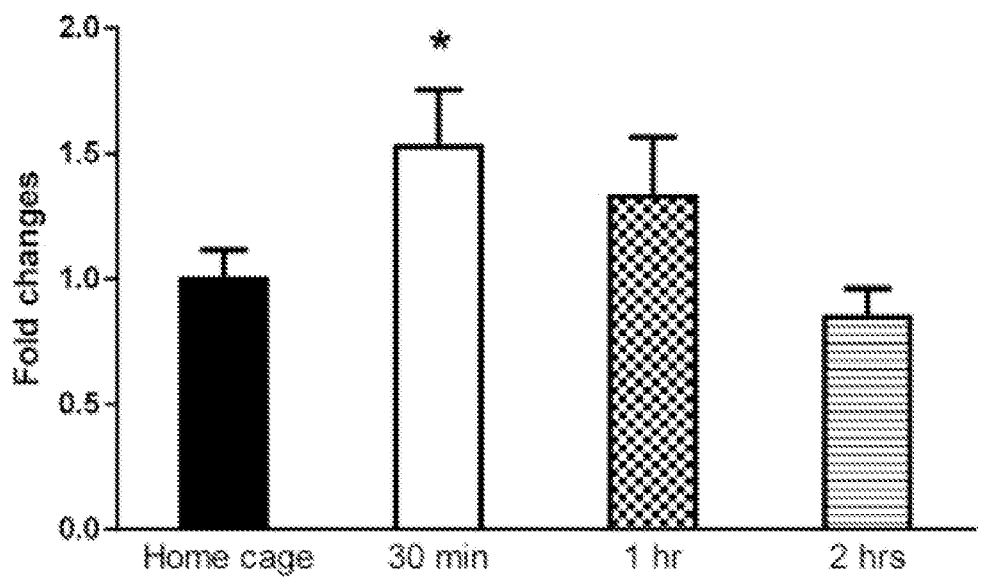
FIG. 1A show data indicating Tac2 mRNA levels are rapidly up-regulated in the amygdala during fear consolidation 30 minutes after fear conditioning.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "combination with" when used to describe administration with an additional treatment means that the agent may be administered prior to, together with, or after the additional treatment, or a combination thereof.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g., patient) is cured and the condition or disease is eradicated. Rather, embodiments, of the present disclosure also contemplate treatment that merely reduces symptoms, and/or delays conditions or disease progression.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxyl group. Contemplated derivative include switching carbocyclic, aromatic or phenyl rings with heterocyclic rings or switching heterocyclic rings with carbocyclic, aromatic or phenyl rings, typically of the same ring size. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, all hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxyl, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

In the present context, salts include pharmaceutical acceptable acid addition salts, pharmaceutically acceptable metal salts, ammonium and alkylated ammonium salts. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

A Role for Tac2, NkB and Nk3 Receptor in Normal and Dysregulated Fear Memory Consolidation The tachykinins refer to two peptides encoded in rodents by the Tachykinin 1 (Tac1) and Tac2 (TAC3 in humans) genes which are involved in neurotransmission and neuromodulation in the central nervous system. Tac1 encodes a precursor protein that produces two peptides, substance P (SP) and neurokinin A (NkA), whereas Tac2/TAC3 encodes neurokinin B (NkB). SP and NkA are implicated in fear processes and PTSD. Clinical trials with pharmaceutical agents targeting the Tac1 pathway have not previously shown beneficial effects in PTSD treatment (Dunlop et al., 2012). A possible explanation for this lack of effect is that the SP and NkA receptors (Neurokinin 1 receptor, Nk1R, and Neurokinin 2 receptor, Nk2R) are widely expressed in the brain—when administering drugs that specifically target Nk1 and Nk2 they interact with multiple brain regions affecting multiple functions. In contrast, the expression of Tac2, NkB, and its specific receptor, Neurokinin 3 receptor (Nk3R), are relatively restricted in rodents to brain regions that regulate emotion, such as the amygdala. Nk3R is a G-protein coupled tachykinin receptor that binds NkB with highest affinity. Nk3R couples to the pertussis toxininsensitive-G proteins Gq/G11, the activation of which results in the production of inositol triphosphate and diacylglycerol, and the activation of protein kinase C. TAC3 and Nk3R are expressed in the equivalent areas in rhesus monkeys and humans.

Experiments disclosed herein indicate that (1) the Tac2 gene is dynamically regulated during the consolidation of conditioned fear within the central amygdala (CeA) and (2) Nk3R activation is required for normal consolidation of fear memory formation in mice. Increased expression of the Tac2 gene, NkB peptide and activation of Nk3R may be involved in stress sensitization and over-consolidation of fear. In contrast, genetic silencing of Tac2-expressing neurons impairs fear consolidation. Blockade of this pathway may provide for a novel therapeutic approach for disorders with altered fear learning such as PTSD.

Experiments indicate that enhanced Tac2 gene expression in fear models enhanced NkB production in the amygdala, binding to Nk3R, and promote fear memory consolidation. This up-regulation of Tac2 mRNA levels primarily within the CeM leaves open several possible non-mutually exclusive mechanistic scenarios, although it is not intended that embodiments of this disclosure be limited to any particular mechanism. It may be that the Tac2 gene synthesizes NkB in the CeM amygdala, acting on local Nk3R within the CeM specifically. Another possibility is that Tac2 mRNA and/or NkB are transported from the CeM to other nuclei within the amygdala such as CeL, CeC or BLA where they bind to the Nk3R. Experiments herein indicate that amygdala cell culture with osanetant, a reported an antagonist of Nk3R, increases Nk3R mRNA levels. One interpretation of these results is that osanetant antagonizes amygdale Nk3R and due to its decreased availability, e.g., Nk3R mRNA is increased to synthesize more Nk3R in a compensatory manner. This data indicates a specific role of Tac2 gene, via NkB activation of Nk3R in fear consolidation within the CeA.

The CeM is under tonic inhibitory control from CeL by a shift in the balance of activity between the $CeL_{on}$ and $CeL_{off}$ neurons during FC. $CeL_{on}$ neurons present an excitatory response to the conditioned stimulus during fear expression whereas $CeL_{off}$ show an inhibitory response. Thus, $CeL_{on}$ inhibition leads to inhibited FC and $CeL_{off}$ facilitates FC. Specifically, $CeL_{off}$ neurons largely overlap with PKCd+ neurons Moreover, we also show that Tac2 gene is not colocalized with Enk in the CeM. Enk is co-localized with PKCd in the CeL and specific CeA-Enk deletion decreases fear expression during FC without affecting fear memory consolidation. Thus, the Tac2-CeM neuronal population appears to be independent of, and complementary to, other previously described neuronal populations involved in FC. The GAD65 peptide, abundantly found at nerve terminals and synapses, plays a role in GABA neurotransmission. Additionally, CaMKII is a well-known marker for synaptic plasticity. Thus, the colocalization of Tac2 mRNA levels and GAD65 and CaMKIIα peptides in the CeM suggest that Tac2 gene may have a role in neurotransmission within the GAD65 and CaMKIIα expressing neurons, in agreement with data disclosed herein that this CeM population may be involved in fear memory consolidation.

Data disclosed herein indicates the use of the Nk3R antagonist osanetant as a pharmacological agent to block fear memory consolidation shortly after exposure to a trauma.

Osanetant prevented the up-regulation of the Adcyap1r1 gene, which encodes the PAC1 receptor. The PACAP-PAC1R pathway is involved in PTSD, fear conditioning, amygdala excitatory neurotransmission and stress [Ressler et al. (2011). Post-traumatic stress disorder is associated with PACAP and the PAC1 receptor. Nature 470, 492-497; Almli et al., (2013); and Stevens et al. report PACAP receptor gene polymorphism impacts fear responses in the amygdala and hippocampus. Proceedings of the National Academy of Sciences of the United States of America, 2014, 111, 3158-3163. ADCYAP1R1 genotype associates with post-traumatic stress symptoms in highly traumatized African-American females. American journal of medical genetics Part B, Neuropsychiatric genetics: the official publication of the International Society of Psychiatric Genetics 162B, 262-272; Cho et al. (2012). Pituitary adenylate cyclase-activating polypeptide induces postsynaptically expressed potentiation in the intra-amygdala circuit. The Journal of neuroscience: the official journal of the Society for Neuroscience 32, 14165-14177; Hashimoto et al. (2011). PACAP is implicated in the stress axes, Current pharmaceutical design 17, 985-989; Uddin et al. (2013). Adcyap1r1 genotype, posttraumatic stress disorder, and depression among women exposed to childhood maltreatment. Depression and anxiety 30, 251-258].

In summary, these studies provide a new understanding of the role of the Tac2 gene and the CeM in fear processing and provide an approach to intervention for fear-related disorders for human subjects by administering NK3 receptor antagonists.

Neurokinin Receptor Antagonist

Numerous neurokinin 3 receptor antagonist are reported. See e.g., U.S. Pat. No. 7,560,549, entitled, "Sulfonyloxy derivatives," U.S. Pat. No. 8,138,334, entitled, "Substituted oxa-diaza-spiro-[5.5]-undecanone derivatives and their use as neurokinin antagonists," U.S. Pat. No. 7,544,694 entitled, "Substituted diaza-spiro-[5.5]-undecane derivatives and their use as neurokinin antagonists," U.S. Pat. No. 7,435,736 entitled, "Substituted 1-piperidin-4-yl-4-azetidin-3-yl-piperazine derivatives and their use as neurokinin antagonists," and U.S. Pat. No. 7,410,970. All of the compounds disclosed are contemplated for uses disclosed herein.

In certain embodiments, the neurokinin 3 receptor antagonist is (R)—N—{{3-[1-Benzoyl-3-(3,4-dichlorophenyl)piperidin-3-yl]prop-1-yl}-4-phenylpiperidin-4-yl}-N-methylacetamine, derivatives or salts thereof.

In certain embodiments the derivative is a compound of the following formula

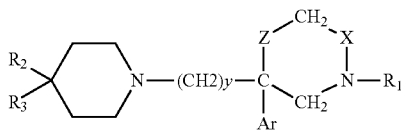

or salts or derivatives thereof wherein

X is $CH_2$, or C=O;
Z is $CH_2$ or O;
y is 2 or 3;
Ar represents a phenyl mono- or di-substituted with a halogen atom;
$R_1$ represents a phenyl or benzoyl that is un-substituted or substituted once or twice with one or two substituents independently chosen from a halogen atom, a ($C_1$-$C_4$)alkyl and a ($C_1$-$C_4$)alkoxy;
$R_2$ represents:
a pyridyl;
a phenyl that is un-substituted or substituted once or twice with one or two substituents independently chosen from a halogen atom, a ($C_1$-$C_4$)alkyl, a ($C_1$-$C_4$)alkoxy, a trifluoromethyl group and a trifluoromethoxy group;
a benzyl that is un-substituted or substituted on the phenyl once or twice with one or two substituents independently chosen from a halogen atom, a ($C_1$-$C_4$)alkyl, a ($C_1$-$C_4$)alkoxy, a trifluoromethyl group and a trifluoromethoxy group;
$R_2$ may also represent:
a heterocyclyl chosen from azetidine, pyrrolidine, piperidine, morpholine, thiomorpholine or perhydroazepine when $R_3$ represents a cyano or a group —$CONR_{11}R_{12}$;
$R_3$ represents a group chosen from:
(1) ($C_1$-$C_4$) alkyl;
(2) ($C_1$-$C_4$) alkylcarbonyl;
(3) cyano;
(4) —$(CH_2)_q$—OH;
(5) —$(CH_2)_q$—O—($C_1$-$C_4$)alkyl;
(6) —$(CH_2)_q$—O—CO—$R_4$;
(7) —$(CH_2)_q$—O—CO—NH—($C_1$-$C_4$)alkyl;
(8) —$NR_5R_6$;
(9) —$NR_7COR_8$;
(10) —$(CH_2)_q$—$NR_7COR_8$;
(11) —$(CH_2)_q$—$NR_7COOR_9$;
(12) —$(CH_2)_q$—$NR_7SO_2R_{10}$;
(13) —$(CH_2)_q$—$NR_7CONR_{11}R_{12}$;
(14) —$CH_2NR_{13}R_{14}$;
(15) —$CH_2$—$CH_2NR_{13}R_{14}$;
(16) —COOH;
(17) —COO—($C_1$-$C_4$) alkyl;
(18) —$CONR_{11}R_{12}$;
(19) —$CH_2$—COOH;
(20) —$CH_2$—COO—($C_1$-$C_4$)alkyl;
(21) —$CH_2$—$CONR_{11}R_{12}$;
(22) —O—$CH_2CH_2OR_{15}$;
(23) —$NR_7COCOR_{16}$;
(24) —$CONR_7$—$NR_{17}R_{18}$;

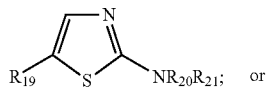
(25)

or

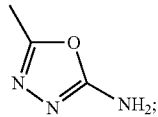
(26)

q is 0, 1 or 2;
$R_4$ represents a ($C_1$-$C_4$)alkyl; a ($C_3$-$C_7$)cycloalkyl that is un-substituted or substituted with one or more methyl groups; a phenyl, or a pyridyl;
$R_5$ and $R_6$ each independently represent a hydrogen atom or a ($C_1$-$C_4$)alkyl; $R_6$ may also represent a ($C_3$-$C_7$)cycloalkylmethyl, a benzyl or a phenyl; or $R_5$ and $R_6$, together with the nitrogen atom to which they are attached, constitute a heterocycle chosen from azetidine, pyrrolidine, piperidine, morpholine thiomorpholine, perhydroazepine or piperazine that is un-substituted or substituted in position 4 with a ($C_1$-$C_4$)alkyl;
$R_7$ represents a hydrogen atom or a ($C_1$-$C_4$)alkyl;
$R_8$ represents a hydrogen atom; a ($C_1$-$C_4$)alkyl; a vinyl; a phenyl; a benzyl; a pyridyl; or a ($C_3$-$C_7$)cycloalkyl that is un-substituted or substituted with one or more methyl groups; a furyl; a thienyl; a pyrrolyl; an imidazolyl;
or $R_7$ and $R_8$ together represent a group —$(CH_2)_p$—;
p is 3 or 4;
$R_9$ represents a ($C_1$-$C_4$) alkyl or a phenyl;
or $R_7$ and $R_9$ together represent a group —$(CH_2)_n$—;
n is 2 or 3;
$R_{10}$ represents a ($C_1$-$C_4$) alkyl or an amino that is free or substituted with one or two ($C_1$-$C_4$)alkyls; a phenyl that is un-substituted or substituted one or more times with a substituent chosen from: a halogen atom, a ($C_1$-$C_4$)alkyl, a trifluoromethyl, a hydroxyl, a ($C_1$-$C_4$)alkoxy, a carboxyl, a ($C_1$-$C_4$)alkoxycarbonyl, a ($C_1$-$C_4$)alkylcarbonyloxy, a cyano, a nitro, an amino that is free or substituted with one or two ($C_1$-$C_4$)alkyls, the said substituents being identical or different;
$R_{11}$ and $R_{12}$ each independently represent a hydrogen or a ($C_1$-$C_4$) alkyl; $R_{12}$ may also represent a ($C_3$-$C_7$)cycloalkyl, a ($C_3$-$C_7$)cycloalkylmethyl, a hydroxyl, a ($C_1$-$C_4$)alkoxy, a benzyl or a phenyl; or $R_{11}$ and $R_{12}$, together with the nitrogen atom to which they are attached, constitute a heterocycle chosen from azetidine, pyrrolidine, piperidine, morpholine thiomorpholine and perhydroazepine;
or $R_7$ and $R_{12}$ together represent a group —$(CH_2)_m$—;

m is 2 or 3;

$R_{13}$ and $R_{14}$ each independently represent a hydrogen atom or a $(C_1-C_4)$alkyl; $R_{10}$ may also represent a $(C_3-C_7)$ cycloalkylmethyl or a benzyl;

$R_{15}$ represents a hydrogen atom; a $(C_1-C_4)$alkyl; a formyl; a $(C_1-C_4)$alkylcarbonyl;

$R_{16}$ represents a $(C_1-C_4)$alkoxy;

$R_{17}$ and $R_{18}$ each independently represent a hydrogen atom or a $(C_1-C_4)$alkyl;

or alternatively $R_{17}$ and $R_{18}$, together with the nitrogen atom to which they are attached, constitute a heterocycle chosen from pyrrolidine, piperidine and morpholine;

$R_{19}$ represents a hydrogen atom or a $(C_1-C_4)$alkyl; and $R_{20}$ and $R_{21}$ each independently represent a hydrogen atom or a $(C_1-C_4)$ alkyl; $R_{21}$ may also represent a formyl or a $(C_1-C_4)$alkylcarbonyl.

In certain embodiments, X is $CH_2$, Z is $CH_2$, Ar represents a phenyl di-substituted with a halogen atom, y is 3, and $R_1$ is benzoyl.

In certain embodiments, the neurokinin 3 receptor antagonist is talnetant, 3-hydroxy-2-phenyl-N-(1-phenylpropyl) quinoline-4-carboxamide, 3-methyl-2-phenyl-N-(1-phenylpropyl) quinoline-4-carboxamide, derivative, or salt thereof. WO95/32948 discloses a range of quinoline derivatives, including talnetant as NK3 antagonists. Other reported NK3 antagonists are reported in WO 2006/130080, WO 2006/050991, WO 2006/050992, WO 2008/131779, WO 2009/130240. All of the compounds disclosed are contemplated for uses disclosed herein.

Methods of Use

In certain embodiments, the disclosure relates to methods of treating or preventing conditioned fear comprising administering an effective about neurokinin 3 receptor antagonist to a subject in need thereof. In certain embodiments, the subject is diagnosed with Post-Traumatic Stress Disorder. Posttraumatic stress disorder (PTSD) is defined by DSM-IV as an anxiety disorder that an individual may develop following exposure to a traumatic event, and is characterized by (1) re-experiencing the traumatic event, such as recurrent nightmares, intrusive recollections of the event, flashbacks, physiological and psychological responses to internal or external cues relating to the event, etc; (2) persistent avoidance of thoughts, people or places associated with the event; (3) numbing of general responsiveness such as emotional detachment, restricted affect or loss of interest in activities; and (4) persistence of increased arousal such as exaggerated startle response, hypervigilence, irritability, difficulty sleeping, etc. In certain embodiments, the disclosure contemplates a subject with conditioned fear as characterized by re-experiencing the traumatic event; e.g., recurrent nightmares, intrusive recollections of the event, flashbacks, recurring daily, bi-daily, or weekly; and one, two, or all of symptoms (2)-(4). In certain embodiments, the subject is at high-risk of PTSD such as a combat veteran, a victim of criminal mayhem, or a rape victim.

In certain embodiments, the neurokinin 3 receptor antagonist is administered in combination with a second active agent such as an anti-depressant. In certain embodiments, the agent is sertraline, paroxetine, fluoxetine, citalopram, baclofen, modafinil, eszopiclone, hydrocortisone, varenicline, dexamethasone or combinations thereof.

In certain embodiments, the neurokinin 3 receptor antagonist is administered within an hour of or within a day of experiencing a traumatic event.

In certain embodiments, the neurokinin 3 receptor antagonist is administered within (before and/or after) an hour, two hours, three hours, 1 day, 2 days, or a week of experiencing a traumatic event. In certain embodiments, the traumatic event is that subject viewed the death of a human. In certain embodiments, the traumatic event is that subject viewed the body of a human in which at least one limb of the subject was separated from the body of a human.

In certain embodiments, the neurokinin 3 receptor antagonist is administered at the time of or within (before and/or after) an hour, two hours, three hours, 1 day, 2 days, or a week of psychotherapy, cognitive behavioral therapy, exposure therapy, cognitive restructuring, or stress inoculation training.

The methods of the disclosure encompass the use of any type of psychotherapy that is suitable and may be conducted in one or more sessions. Suitable methods of psychotherapy include behavior psychotherapy such as exposure-based psychotherapy, cognitive psychotherapy including cognitive training and psychodynamically oriented psychotherapy (see, for example, Foa (2000) J. Clin. Psych. 61(suppl. 5):43-38).

"Psychotherapy" refers broadly to forms of psychiatric treatment which employ specialized communication techniques practiced by a properly trained physician, counselor, or clinician for the purpose of curing or reducing or alleviating a behavioral disorder of a patient and improving the patient's emotional, social, and/or mental health.

One method of psychotherapy specifically contemplated is the use of virtual reality (VR) exposure therapy to treat a psychiatric disorder using the combination therapy protocol of the disclosure. VR therapy to treat certain conditions such as PTSD in, for example, Vietnam veterans (Rothbaum et al. 30 (1999) J. Trauma Stress 12(2):263-71) or rape victims (Rothbaum et al. (2001) J. Trauma Stress 14(2):283-93), one embodiment of the present disclosure specifically contemplates the use of such VR exposure psychotherapy in combination with a compounds as described elsewhere herein to treat a psychological condition.

The compound may be administered in a composition suitable for oral, rectal, topical, and parenteral (including subcutaneous, intramuscular, and intravenous) administration, although the most suitable route in any given case will depend on the particular subject, and nature and severity of the conditions for which the active ingredient is being administered. The pharmaceutical compositions may be conveniently presented in unit dosage form and prepared by any of the methods well known in the art of pharmacy.

As used herein, a "therapeutically effective amount" is an amount of the compound which, depending on the selected mode, frequency and duration of administration, and the desired results. A therapeutically effective amount for the treatment of a psychiatric disorder is one that, depending on the selected mode, frequency and duration of administration, inhibits the occurrence or recurrence of the psychiatric disorder in the patient or alleviates one or more symptoms of the disorder in the patient. Effective amounts to inhibit the occurrence or recurrence of the psychiatric disorder in a patient are prophylactic dosages preferably administered in small amounts over a prolonged course of preventive therapy to patients at risk of developing the disorder. Determination of effective dosages in this case is typically based on human clinical trials and is approximated by determining effective dosages that significantly reduce the occurrence or incidence of the psychiatric disorder in model patients and administration protocols.

The actual dosage will vary according to factors such as the disease state, age, and weight of the individual, and the ability of compound to elicit a desired response in the individual. Dosage regimens may be adjusted to provide an optimum therapeutic response. A therapeutically effective amount is also one in which any toxic or detrimental side effects of the compound are outweighed by therapeutically beneficial effects.

In certain embodiments, the neurokinin 3 receptor antagonist is (R)—N—{{3-[1-Benzoyl-3-(3,4-dichlorophenyl)piperidin-3-yl]prop-1-yl}-4-phenylpiperidin-4-yl}-N-methylacetamine, or salt thereof, and the subject is a human and an effective amount is a daily dose of about 25 mg per day. In certain embodiments, the daily dose is between 10 and 40 mg per day.

In certain embodiments, the subject is a human and an effective amount is a daily dose of about 15 mg per day. In certain embodiments, the daily dose is between 5 and 25 mg per day.

In certain embodiments, the subject is a human and an effective amount is a daily dose of about 35 mg per day. In certain embodiments, the daily dose is between 25 and 45 mg per day.

In certain embodiments, the subject is a human and an effective amount is a daily dose of about 50 mg per day. In certain embodiments, the daily dose is between 25 and 75 mg per day.

In certain embodiments, the subject is a human and an effective amount is a daily dose of about 75 mg per day. In certain embodiments, the daily dose is between 25 and 125 mg per day. In certain embodiments, the daily dose is between 50 and 100 mg per day.

In certain embodiments, the subject is a human and an effective amount is a daily dose of about 100 mg per day. In certain embodiments, the daily dose is between 25 and 200 mg per day. In certain embodiments, the daily dose is between 50 and 150 mg per day. In certain embodiments, the daily dose is between 75 and 125 mg per day.

In certain embodiments, the subject is a human and an effective amount is a daily dose of about 150 mg per day. In certain embodiments, the daily dose is between 25 and 250 mg per day. In certain embodiments, the daily dose is between 50 and 250 mg per day. In certain embodiments, the daily dose is between 100 and 200 mg per day. In certain embodiments, the daily dose is between 125 and 175 mg per day.

In certain embodiments, the subject is a human and an effective amount is a daily dose of about 200 mg per day. In certain embodiments, the daily dose is between 100 and 300 mg per day. In certain embodiments, the daily dose is between 150 and 250 mg per day.

EXPERIMENTAL

Tac2 is Involved in Fear Learning

Figure 1B:
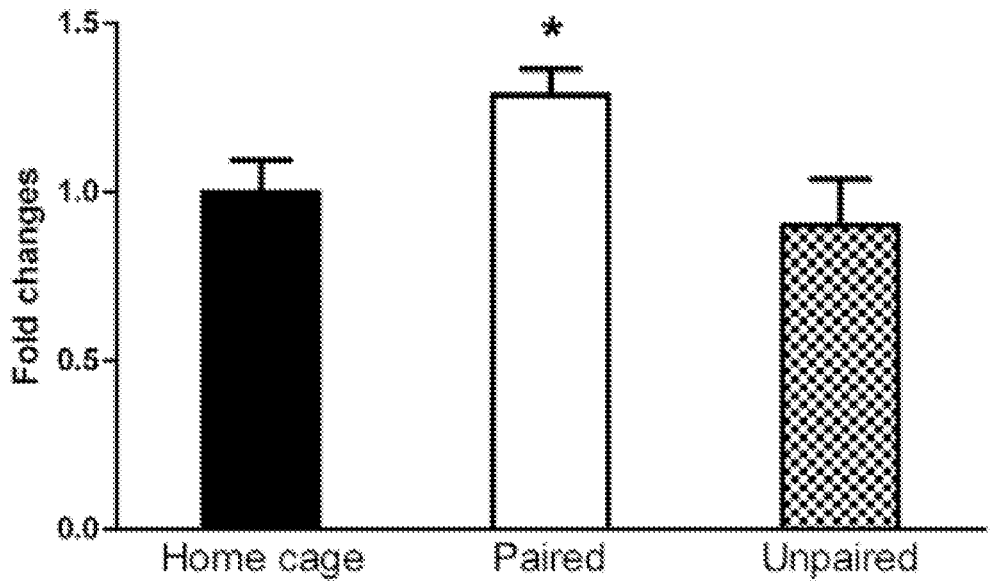
FIG. 1B shows data indicating Tac2 up-regulation occurs when the conditioned stimulus (acoustic tone) and the unconditioned stimulus (electric footshock) are paired but not when they are unpaired.

Using amygdala tissue punches from mice that had been sacrificed 30 minutes or 2 hours after auditory fear conditioning (FC) (CS, acoustic tone; US, electric footshocks), an mRNA microarray was performed. Using average linkage hierarchical clustering, the microarray heat map shows differential gene regulation at 30 minutes and at 2 hours after fear learning, which is an important period for consolidation of fear memories, FIG. 1A. FDR was calculated with SAM 4.01 using a standard 5% cutoff criteria. The cutoff criteria was set with an FDR at the 1.3 fold level for the 2 hrs after fear conditioning (FC) group, since with the more conservative 1.5 fold cutoff used in the 30 min after FC group, no genes were initially identified. From the top candidates of this microarray, Tac2 was selected because it is specifically highly expressed in the amygdala and belongs to a 'druggable' pathway with available agonists and antagonists which cross the blood-brain barrier and can be used systemically. Understanding and manipulating the Tac2 pathway was evaluated. Independent replication studies with additional fear conditioned mice show that Tac2 is rapidly upregulated at 30 minutes after FC, returning to basal levels at 2 hours (ANOVA $F_{3,28}$=5.014, P≤0.01, Post-hoc *P≤0.05 vs Home Cage (HC) and 2 hrs, FIG. 1A). Moreover, in an additional replication, Tac2 mRNA upregulation only occurred when the conditioned and unconditioned stimuli are paired, but not when they are unpaired, suggesting that within this paradigm, Tac2 increased expression is specific to associative cued fear learning and independent of non-specific stress and/or contextual learning (ANOVA $F_{2,36}$=3.93, P≤0.05, Posthoc *P≤0.05 vs HC and unpaired, FIG. 1B).

Tac2, NkB and Nk3R in the Amygdala

Radioactive in situ hybridization indicates that the areas where Tac2 gene is expressed are quite specific and limited within in the mouse brain: bed nucleus of the stria terminalis, hypothalamus, habenula, central amygdala (CeA), zona incerta and medial mammillary nucleus. Tac2 is highly expressed in the CeA within the amygdala with no expression in the basolateral amygdala (BLA) nor lateral amygdala (LA). The highest expression of Tac2 within the CeA occurs in the medial subdivision of the central amygdaloid nucleus (CeM), whereas lower expression is observed in the centro-lateral (CeL) and centro-central (CeC) amygdala.

Recently, specific cell populations within the central nucleus have received attention for distinct roles in fear learning. For example, PKCd has been suggested to be part of a microcircuit in which the CeL amygdale neurons inhibit neuronal output to the CeM during the conditioned stimulus, which drives fear expression, called $CeL_{off}$ units. Moreover, around 40% of Protein Kinase C Delta (PKCd) expressing neurons also express Enkephalin (Enk) in the CeL. Of note, Enk mRNA levels are increased after FC in the CeL. Since other neuronal populations have been previously related to fear processes in the CeA, it was examined whether Tac2 mRNA colocalized with them suggesting functional interactions. Using double fluorescent in situ hybridization (FISH), Tac2 gene expression was shown to mostly not colocalized with PKCd nor Enk and is expressed primarily within the CeM. Thus, given the lack of colocalization and regional and functional specificity of these cell populations, a subdivision-specific cell population that may be involved in the consolidation of fear memory is identified. The colocalization of Tac2 mRNA levels and the 65-kDa isoform of glutamic acid decarboxylase (GAD-65) peptide in the CeM may provide deeper understanding of the functions of gamma-aminobutyric acid (GABA) in fear learning. CaMKIIα, a neuronal population involved in synaptic plasticity, is also colocalized with Tac2 mRNA in the CeM. Interestingly, GAD65 and CaMKII are associated with the consolidation of fear memories in the amygdala.

Figure 2A:
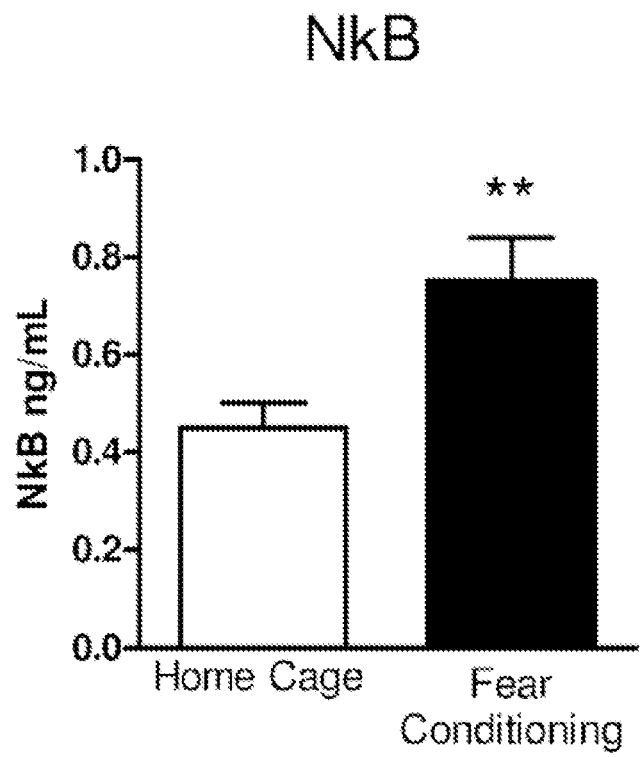
FIG. 2A shows data indicating fear conditioning, expression of Neurokinin B in the amygdala. The Tac2 product, Neurokinin B (NkB) is detected by immunocytochemistry in mouse amygdala cell culture. NkB is highly expressed in the soma and in the dendrites. Red is NkB signal. Blue is neuronal nucleus, NeuN. Immunohisto-chemistry studies show high expression of NkB in the central amygdala (CeA). NkB is up-regulated at 2 hrs in the amygdala after fear conditioning.
Figure 2B:
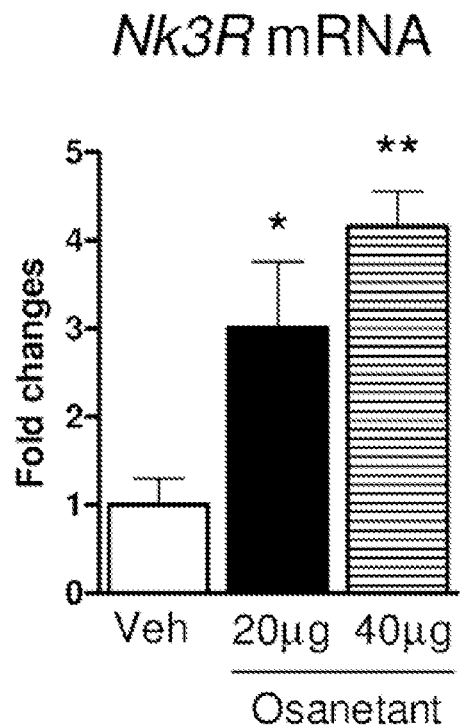
FIG. 2B shows data on Amygdala cell culture with osanetant, a potent and specific neurokinin 3 (Nk3R) antagonist. Incubation with 20 μg and 40 μg of osanetant enhances Nk3R mRNA levels. This suggests that osanetant activates Nk3R and its downstream signaling in the amygdala.

The presence of the NkB peptide in amygdala cell culture was also examined, demonstrating that the peptide is highly present in both soma of neurons and dendrites. Moreover, NkB peptide is also highly expressed in the CeA. Interestingly, NkB is up-regulated in the amygdala 2 hours after FC (Student's t test, t=−2.902, **P≤0.01 Fear Conditioning vs Home Cage, FIG. 2A). The Nk3R antagonist osanetant has already been used in humans in clinical trials for schizophrenia. In amygdala cell culture, osanetant inactivates the Nk3R and leads to a compensatory increase in Nk3R expression as suggested by dose-dependent enhanced Nk3R mRNA levels (ANOVA, $F_{3,5}$=10.014, P≤0.05; Post-hoc *P≤0.05 vs Veh, **P≤0.01 vs Veh, FIG. 2B).

Osanetant and Emotional Learning

Figure 3A:
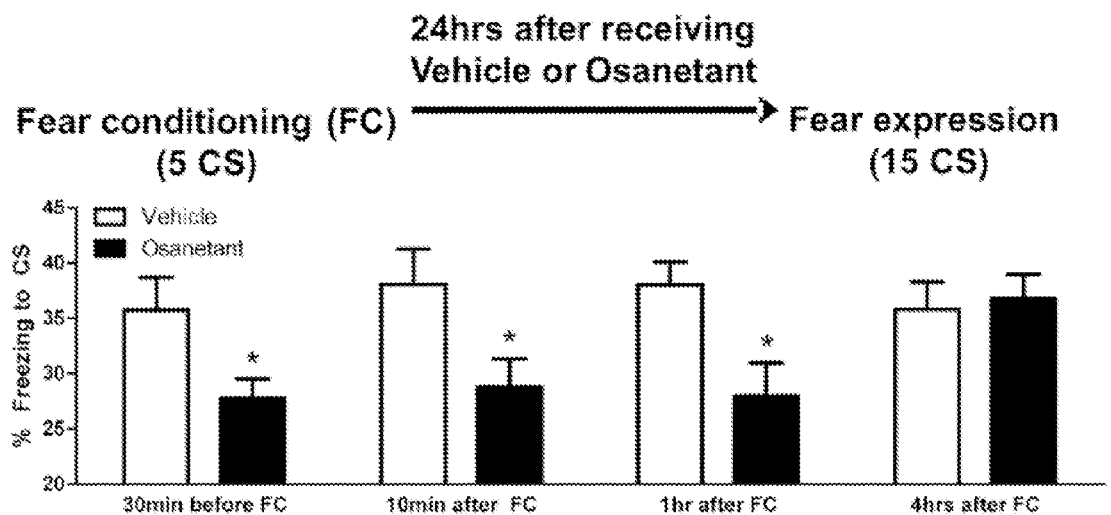
FIG. 3A shows data indicating Nk3R antagonist impairs cued-fear memory consolidation when infused systemically, in the central amygdala and in a PTSD-like mouse model. Osanetant impairs cued-fear memory when given from 30 minutes to up to 1 hour after fear acquisition. The figure shows the time spent in freezing behavior during the fear expression test when the CS is presented.

The above studies indicate that osanetant would target the Nk3R in the amygdale in vivo. Osanetant given systemically, 30 minutes before open field, elevated plus maze and the conditioning chamber elicits no changes in anxiety-like behavior, locomotor activity or electric shock reactivity. Notably, when osanetant is dosed from 30 min before auditory FC up to 1 hour after training it does not affect fear acquisition, but impairs fear memory consolidation as shown by decreased freezing in the fear expression test (FIG. 3A; Student's t test, 30 min t=3.042; 10 minutes after FC, t=2.277; 1 hour after FC, t=2.872; $*P \le 0.05$ vs vehicle).

Figure 3B:
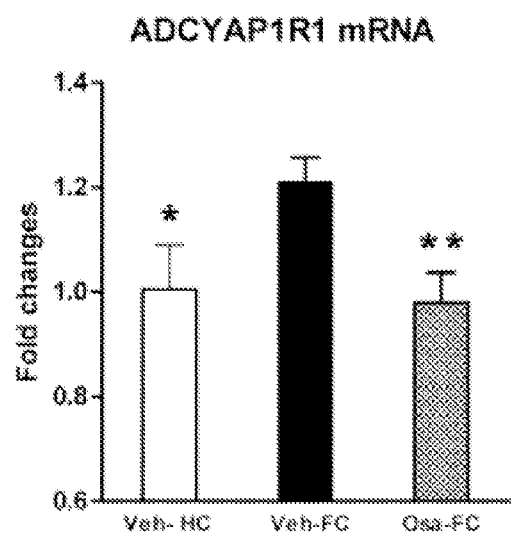
FIG. 3B shows data for osanetant given intraperitoneally 30 minutes before fear conditioning impaired the enhancement of mRNA levels of the Pac1 receptor (Adcyap1r1). The PACAP-PAC1R pathway is associated with PTSD, fear conditioning and stress.
Figure 3C:
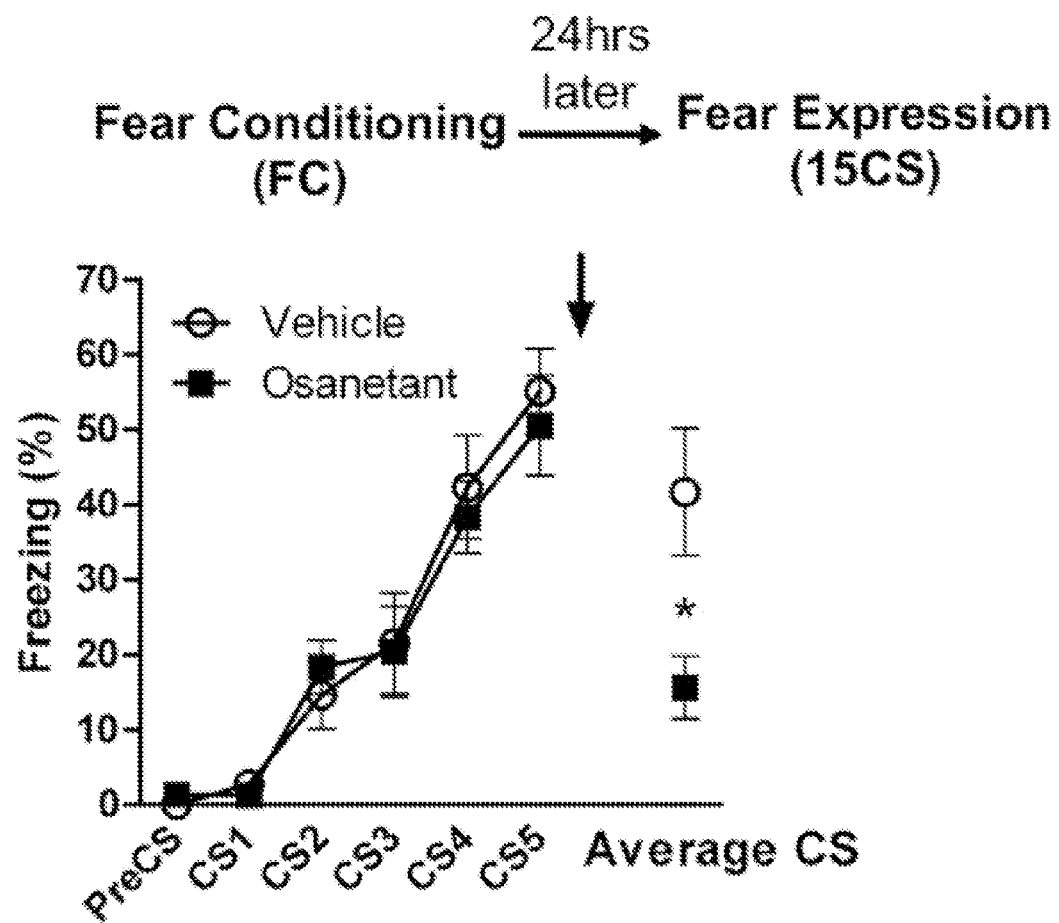
FIG. 3C shows data for osanetant bilaterally injected into the central amygdala immediately after fear conditioning causes impaired fear memory consolidation as shown by lower freezing in the cued-fear expression test.

Recently, the PACAP-PAC1R pathway has been associated with PTSD in humans as well as in animal models. (See Stevens et al., 2014). These reports indicated that expression of the ADCYAP1R1 gene (encoding the PACT receptor) is increased following FC. Osanetant given before FC also normalizes the levels of ADCYAP1R1 mRNA levels in the amygdala (ANOVA $F_{2,31}$=5.541, $P \le 0.01$; Post-hoc $*P \le 0.05$ vs Veh-FC; $**P \le 0.01$ vs Veh-FC, FIG. 3B). These data suggest that inhibition of the Tac2/NKB/Nk3R pathway may prevent activation of a stress-related gene pathway previously associated with PTSD. Concordantly, bilateral infusion of osanetant in the CeA also impairs fear memory consolidation, suggesting that CeA-NK3R are required for the formation for emotional memories (Student's t test; t=2.268, $*P \le 0.05$ vs vehicle, FIG. 3C).

Figure 3D:
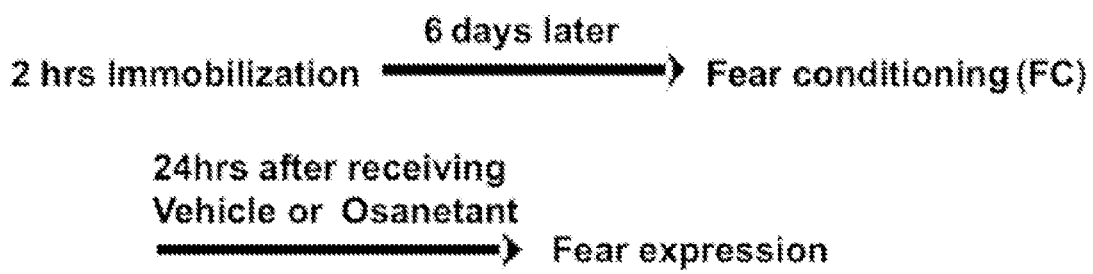
FIG. 3D shows a timeline of the experiment.
Figure 3E:
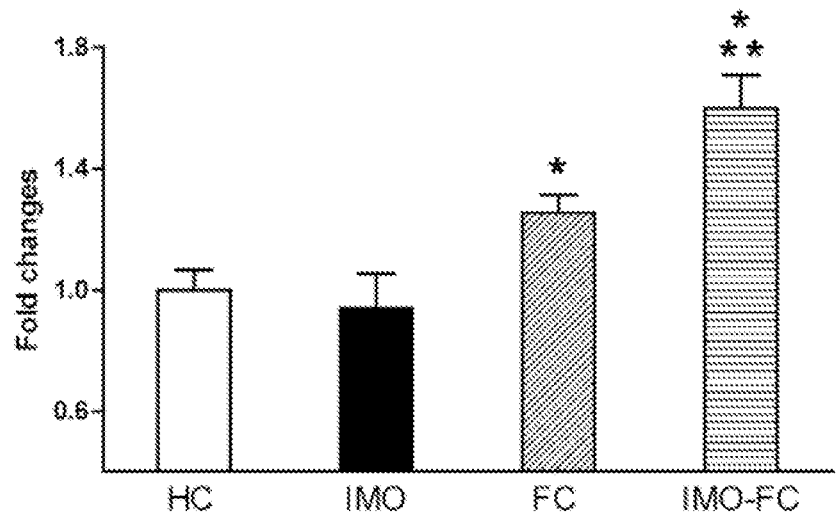
FIG. 3E shows data indicating cued-fear conditioning enhances Tac2 levels 30 minutes after fear conditioning in naïve mice but more robustly in mice with a previous exposure to immobilization to a wooden board (IMO), a PTSD-like model.
Figure 3F:
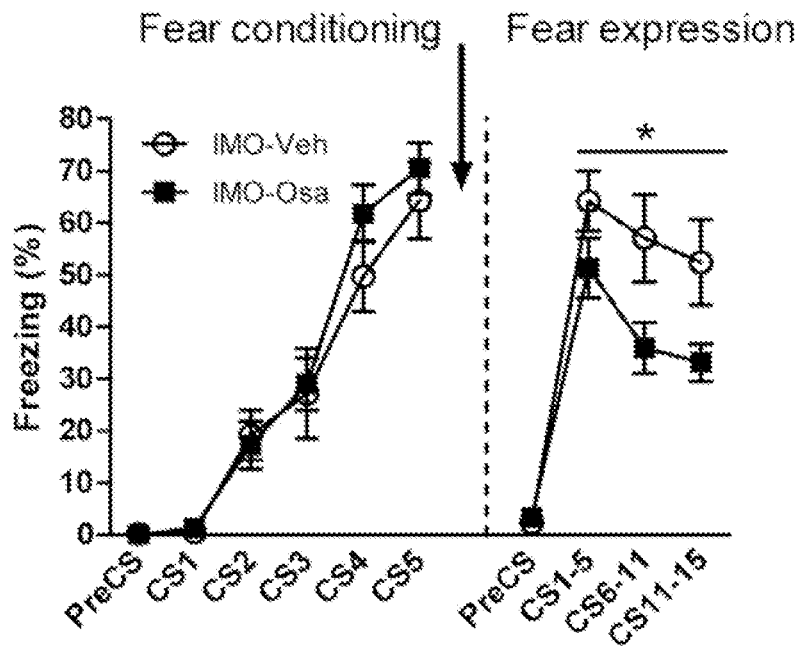
FIG. 3F shows data where Osanetant was given immediately after FC and impaired fear memory consolidation in mice which had been previously exposed to a traumatic stress as shown by reduced freezing in the fear expression test. Veh=vehicle; Osa=osanetant.

Mice exposed for 2 hours to a severe one-time stressor, immobilization to a wooden board (IMO), present long-term PTSD-like symptoms: impaired fear extinction and spatial memory, and enhanced anxiety-like behaviors. Additionally, IMO in rats elicits alterations of the hypothalamic-pituitary-adrenal (HPA) axis which may be similar to the process initiating PTSD in humans. Notably, Tac2 mRNA levels were more robustly upregulated in IMO treated mice than in naïve mice after FC, consistent with enhanced Tac2-dependent fear processing (ANOVA F3,53=6.242, $P \le 0.001$, Post-hoc $*P \le 0.05$ vs HC, $**P \le 0.01$ vs IMO, FIG. 3D). Additionally, osanetant given systemically after FC impaired memory consolidation in IMO treated mice, as shown by decreased freezing in the fear expression test (ANOVA repeated measures F1,13=6.072, $*P \le 0.05$, FIG. 3F). This suggests that Nk3R antagonism reduces enhanced fear memory consolidation in a PTSD-like model.

Tac2 Overexpression and Blockade by Osanetant

Figure 4A:
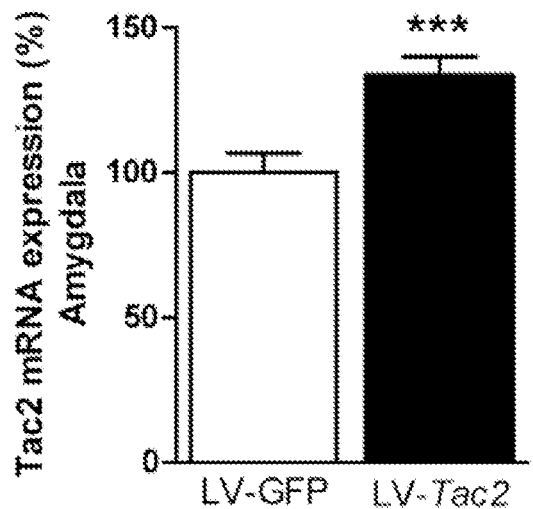
FIG. 4A shows data indicating lentivius Tac2-FUGW causes a 42% overexpression of Tac2 in the central amygdala. The lentivirus GFP-FUGW induces GFP expression but not Neurokinin B (NkB) in Hek293 cells. The lentivirus Tac2-FUGW induces NkB expression in Hek293 cells. Tac2-FUGW or GFP-FUGW were bilaterally infused in the central amygdala and mice were left undisturbed for 14 days.
Figure 4B:
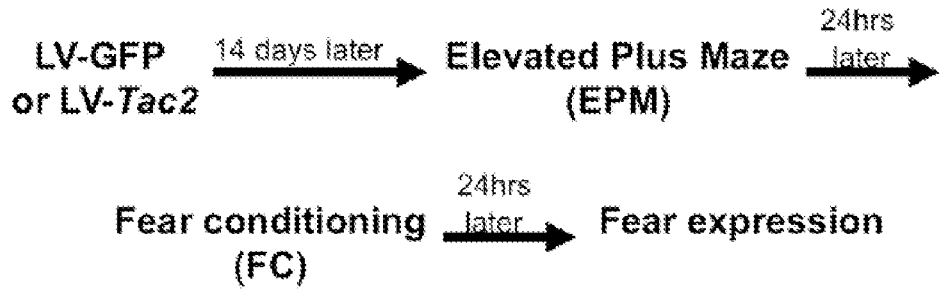
FIG. 4B shows a timeline of an experiment.
Figure 4C:
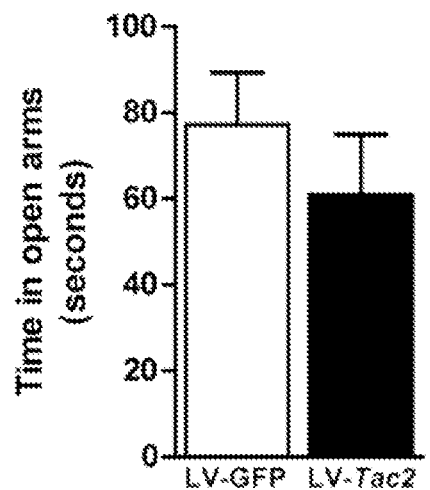
FIG. 4C shows data indicating Tac2 overexpression in the central amygdala does not alter anxiety-like behavior evaluated by the time spent in the open arms in the elevated plus maze.
Figure 4D:
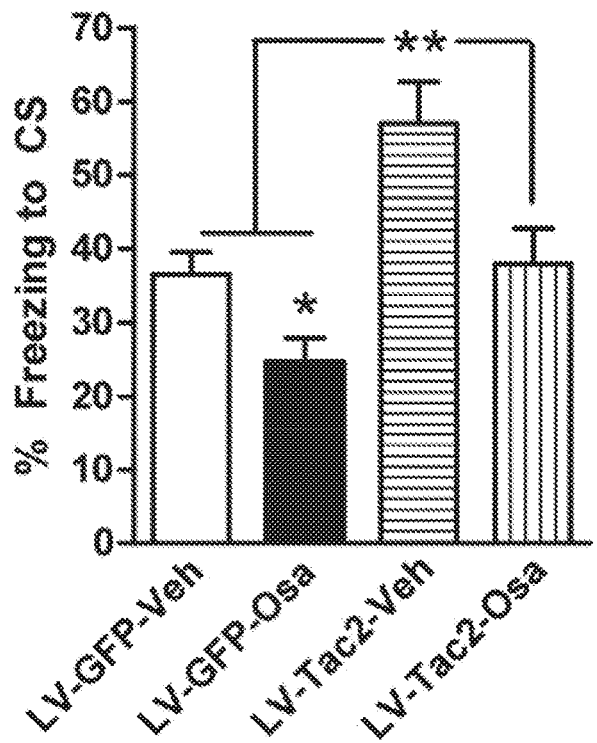
FIG. 4D shows data indicating Tac2 overexpression enhances fear memory consolidation (LV-Tac2-Veh) and osanetant impairs this effect (LV-Tac2-Osa). The lentiviruses GFP-FUGW and Tac2-FUGW causes no changes in fear conditioning. Osanetant or vehicle were given systemically immediately after fear acquisition.

A viral vector was developed to overexpress the Tac2 gene in an inducible fashion within the brain, the lentivirus-Tac2 (LV-Tac2). Its functional expression was tested by infecting HEK 293 cells with the LV-Tac2 compared to control LV-GFP lentiviruses, demonstrating that the NkB peptide was robustly expressed. The behavioral effects of Tac2 overexpression was examined in mice. LV-Tac2 or LVGFP were bilaterally infused in the CeA and 14 days later Tac2 was found to be overexpressed by 42%, as determined by mRNA levels with in situ hybridization, compared to mice that had received LV-GFP (Student's t test; t=-3841, $***P \le 0.001$ vs LV-GFP, FIG. 4A). Mice infected with the LVTac2 or LV-GFP received systemic osanetant or vehicle immediately after FC, and then fear expression was tested 24 hours later. Specific CeA-Tac2 overexpression elicited a significant enhancement of fear memory consolidation. Interestingly, Tac2 overexpression in the CeA did not induce changes in anxiety-like behavior nor fear acquisition. Replicating our previous findings, osanetant impaired fear memory consolidation when given to mice with the control LV-GFP (Post-hoc, $*P \le 0.05$ vs LV-GFP-Veh, FIG. 4D). Additionally, the enhanced fear memory consolidation caused by CeA-Tac2 overexpression was reversed by osanetant (Post-hoc, $**P \le 0.01$ vs LV-Tac2-Osa and LV-GFP-Osa FIG. 4D).

Silencing of Tac2-Expressing Cells and Emotional Learning

Figure 5A:
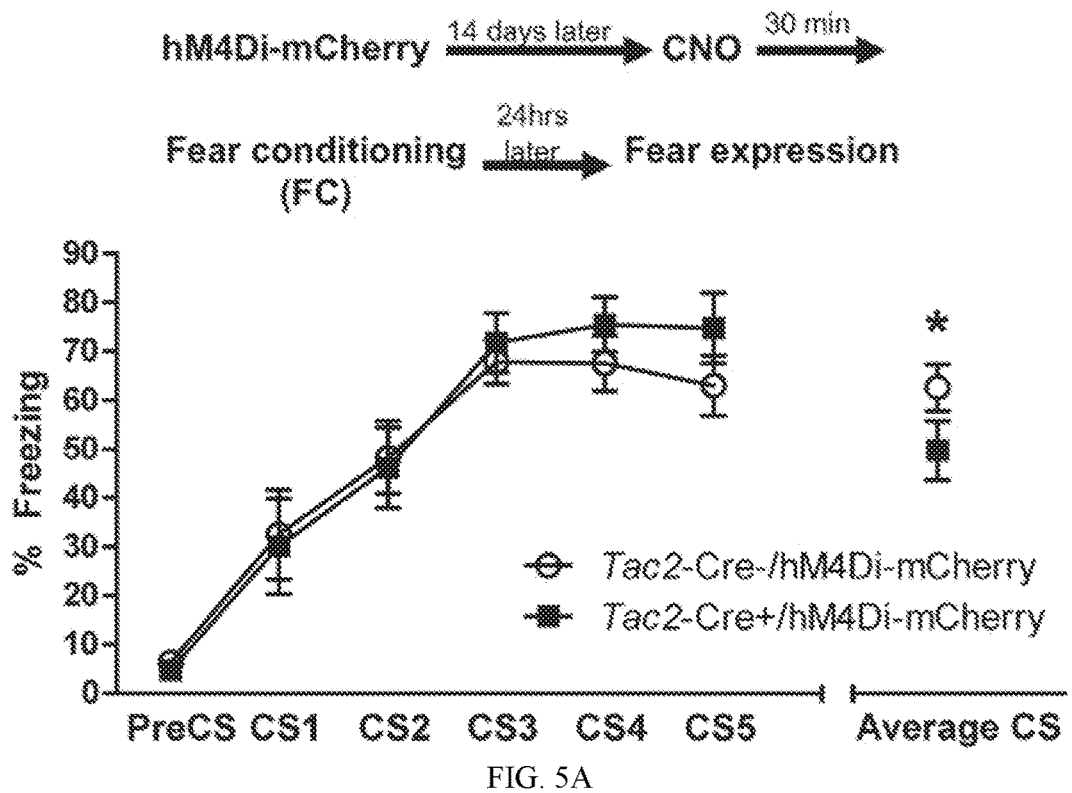
FIG. 5A shows data indicating inducible silencing of Tac2-expressing neurons in the CeA with Gi-DREADD decreases conditioned fear. Tac2-Cre⁻ or Tac2-Cre⁺ mice were infected with the hM4Di-mCherry AAV in the CeA. The Gi receptor was inserted only on the Tac2-Cre cells of Tac2-Cre+ mice, CeM=centro-medial amygdala, CeL=centro-lateral amygdala. CNO was given systemically 30 minutes prior to fear conditioning to Tac2-Cre−/hM4Di-mCherry and Tac2 Cre+/hM4DimCherry. Temporal silencing of the Tac2-expressing neurons in the Tac2-Cre+/hM4Di-mCherry group did not affect freezing during fear acquisition. However, when mice were tested the day after for fear expression without CNO, Tac2-Cre+/hM4Di-mCherry mice showed less conditioned fear. Tac2-Cre−/hM4DimCherry vs Tac2-Cre+/hM4Di-mCherry. Tac2-Cre−/hM4Di-mCherry and Tac2-Cre+/hM4Di-mCherry mice were retrained to a different acoustic tone (CS) without receiving CNO. Both groups equally acquired fear learning and showed similar levels of fear memory consolidation. CNO given 30 minutes before the elevated plus maze showed no effect on Tac2-Cre−/hM4Di-mCherry nor Tac2-Cre+/hM4Di-mCherry in anxiety-like behavior.
Figure 5B:
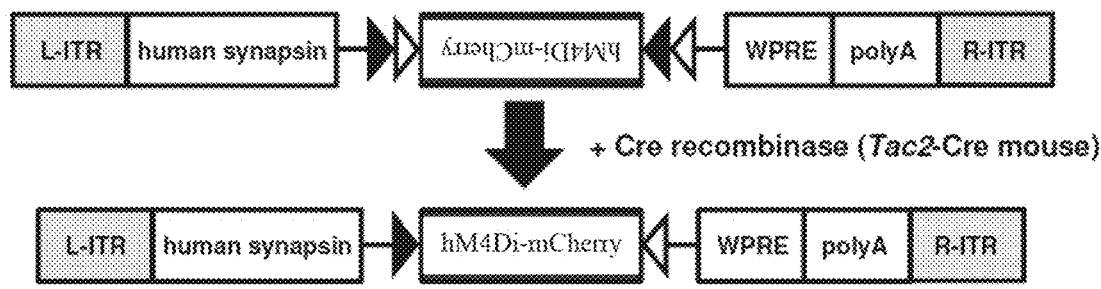
FIG. 5B illustrates the hM4Di-mCherry AAV.
Figure 6A:
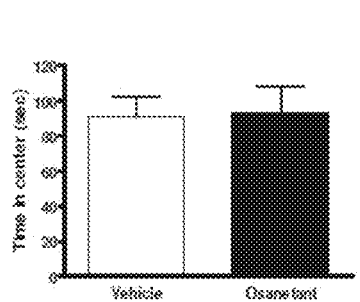
FIG. 6A-G shows data indicating osanetant impairs fear learning with no effects on anxiety, locomotion nor shock reactivity. Different cohorts of mice received systemic osanetant 30 minutes before open field, elevated plus maze or fear conditioning in the startle chamber.
Figure 6B:
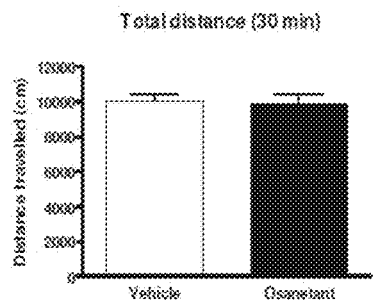
Figure 6C:
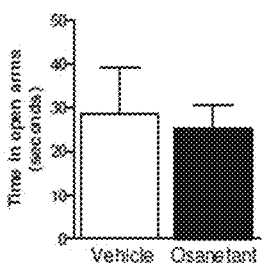
Figure 6D:
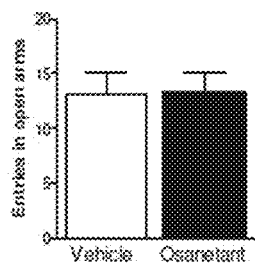
Figure 6E:
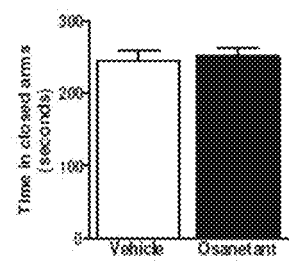
Figure 6F:
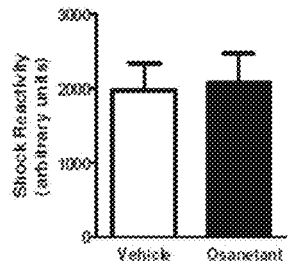
Figure 6G:
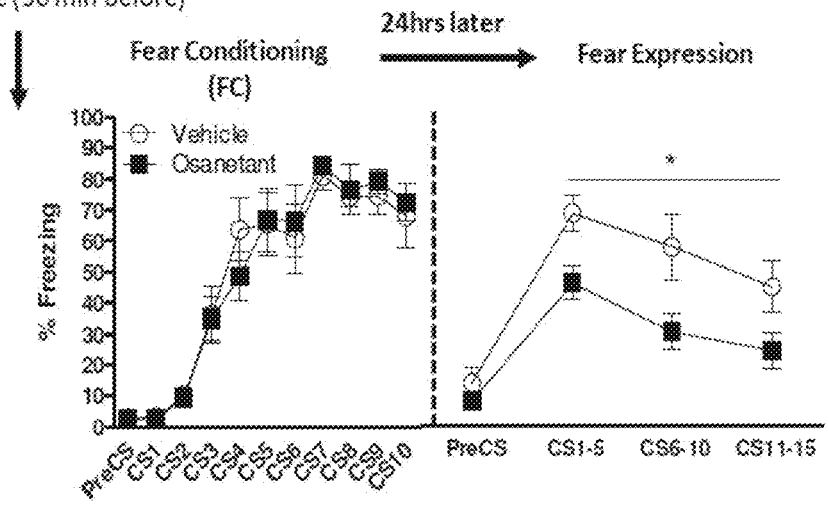
Figure 7:
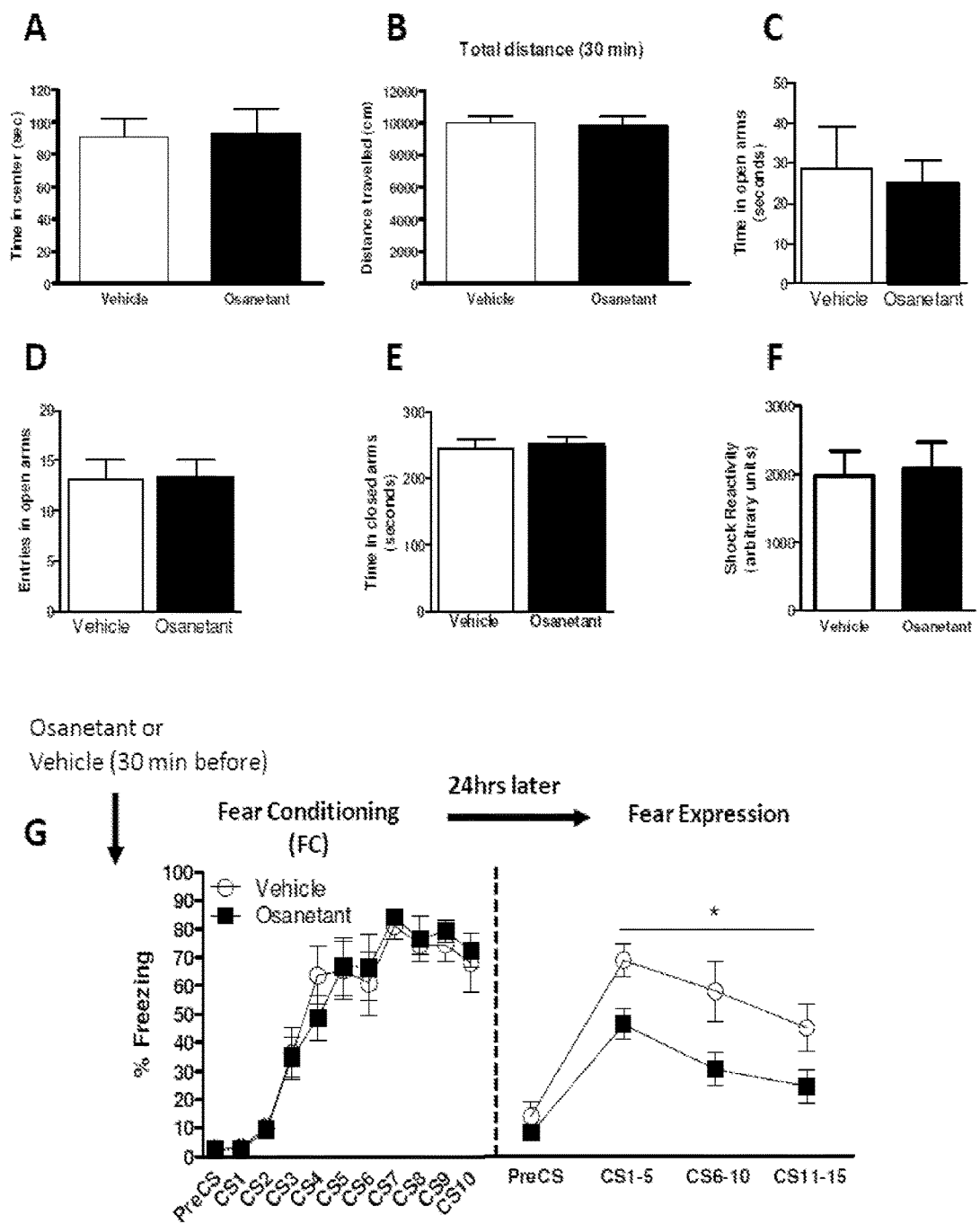

To further understand the role of the Tac2 gene, the activity of neurons expressing this gene in the CeA were temporarily silenced during fear learning using designer receptors exclusively activated by designer drugs (DREADD) technology. The B6.129-Tac2tm1.1(cre) Qima/J (Tac2-cre) (Mar et al., Mol. Brain, 2012, 5, 3) mice were infected with a DREADD Gi-coupled receptor via the pAAV-hSyn-double floxed hM4D-mCherry virus (hM4Di-mCherry AAV). This elicited specific expression of the mCherry reporter in Tac2 cells within the CeA, but not any other area of the brain, suggesting the insertion of the DREADD receptor on the plasma membrane. 14 days later, clozapine-N-oxide (CNO), which binds to the inserted receptor but otherwise is pharmacologically inert, was given systemically 30 minutes before FC in both groups, Tac2-Cre-/hM4Di-mCherry and Tac2-Cre+/hM4Di-mCherry. CNO had no effect on fear acquisition as shown by equivalent amount of freezing in both groups (FIG. 5A). However, when animals were tested for fear expression, 24 hrs later in the absence of CNO, the Tac2-Cre+/hM4Di-mCherry mice presented less freezing, suggesting impaired fear memory consolidation (Student's t test, t=3.257, $**P \le 0.01$ Tac2-Cre-/hM4Di-mCherry vs Tac2-Cre+/hM4Di-mCherry, FIG. 6). This indicates that the animals expressing Tac2-Cre+/hM4Di-mCherry and inducible Gi to temporally silence the activity of Tac2-expressing neurons exhibit significantly less fear consolidation when tested for fear learning. Mice were then retrained with a different CS and a different context in the same FC apparatus, as in previous experiments but without dosing CNO. Tac2-Cre-/hM4Di-mCherry and Tac2-Cre+/hM4Di-mCherry mice showed similar amount of freezing in the FC and fear expression test. This suggests that when Tac2-expressing neurons are not silenced there is normal fear memory consolidation in both Tac2-Cre-/hM4Di-mCherry and Tac2-Cre+/hM4Di-mCherry groups. Moreover, when given CNO, these two groups presented equivalent levels of anxiety-like behavior and pain sensitivity.

The invention claimed is:

1. A method of treating Post-Traumatic Stress Disorder comprising administering an effective amount of (R)—N-{{3-[1-Benzoyl-3-(3,4-dichlorophenyl)piperidin-3-yl]prop-1-yl}-4-phenylpiperidin-4-yl}-N-methylacetamine or salt thereof to a human subject diagnosed with Post-Traumatic Stress Disorder.

2. The method of claim 1, wherein the effective amount is a daily dose of about 25 mg per day.

3. The method of claim 2, wherein the daily dose is between 10 and 40 mg per day.

4. The method of claim 1, wherein (R)—N-{{3-[1-Benzoyl-3-(3,4-dichlorophenyl)piperidin-3-yl]prop-1-yl}-4-phenylpiperidin-4-yl}-N-methylacetamine or salt thereof is administered in combination with a second active agent such as an anti-depressant.

5. The method of claim 4, wherein the agent is sertraline, paroxetine, fluoxetine, citalopram, baclofen, modafinil, eszopiclone, hydrocortisone, varenicline, dexamethasone or combinations thereof.

6. The method of claim 1, wherein (R)—N-{{3-[1-Benzoyl-3-(3,4-dichlorophenyl)piperidin-3-yl]prop-1-yl}-4-phenylpiperidin-4-yl}-N-methylacetamine or salt thereof is administered within an hour of or within a day of experiencing a traumatic event.

7. The method of claim 1, wherein (R)—N-{{3-[1-Benzoyl-3-(3,4-dichlorophenyl)piperidin-3-yl]prop-1-yl}-4-phenylpiperidin-4-yl}-N-methylacetamine or salt thereof is administered at the time of or within an hour of psychotherapy, cognitive behavioral therapy, exposure therapy, cognitive restructuring, or stress inoculation training.

* * * * *